United States Patent
Biris (10) Patent No.: US 8,518,420 B2
(45) Date of Patent: Aug. 27, 2013

(54) ENHANCED BONE CELLS GROWTH AND PROLIFERATION ON TIO2 NANOTUBULAR SUBSTRATES TREATED BY RADIO-FREQUENCY PLASMA DISCHARGE

(75) Inventor: Alexandru S. Biris, Little Rock, AR (US)

(73) Assignee: Board of Trustees of the Universtiy of Arkansas, Little Rock, AR (US)

( * ) Notice: Subject to any disclaimer, the term of this patent is extended or adjusted under 35 U.S.C. 154(b) by 71 days.

(21) Appl. No.: 13/071,637

(22) Filed: Mar. 25, 2011

(65) Prior Publication Data

US 2011/0236435 A1 Sep. 29, 2011

Related U.S. Application Data

(60) Provisional application No. 61/317,834, filed on Mar. 26, 2010.

(51) Int. Cl.
*A61K 9/00* (2006.01)
*C12N 5/00* (2006.01)
*C12N 5/02* (2006.01)
*A01N 63/00* (2006.01)
*A01N 65/00* (2009.01)

(52) U.S. Cl.
USPC ........... 424/400; 435/402; 424/93.7; 977/700

(58) Field of Classification Search
None
See application file for complete search history.

(56) References Cited

U.S. PATENT DOCUMENTS

2010/0028387 A1* 2/2010 Balasundaram et al. ..... 424/400

OTHER PUBLICATIONS

Oh et al. "Significantly accelerated osteoblast cell growth on aligned TiO2 nanotubes." Journal of Biomedical Materials Research Part A 78, No. 1 (2006): 97-103.*
Seunghan Oh et al., Significantly accelerated osteoblast cell growth on aligned TiO2 nanotubes, Journal of Biomedical Materials Research Part A, 2006, 97-103, Wiley Periodicals, Inc.
Satomi, K. et al., Bone-implant interface structures after nontapping and tapping insertion of screw-type titanium alloy endosseous implants, The Journal of Prosthet. Dent., 1988, 59, 339-342.
Linder, L. et al., Clinical aspects of osseointegration in joint replacement, The Journal of Bone and Joint Surg., Aug. 1988, 70-B, 550-555, No. 4.
Puleo, D. A. et al., Osteoblast response to orthopedic implant materials in vivo, J. of Biomed. Mater. Res., 1991, 25, 711-723.
Dalby, M.J. et al., Initial interaction of osteoblasts with the surface of a hydroxyapatite-poly(methylmethacrylate) cement, Biomaterials, 2001, 22, 1739-1747.

(Continued)

*Primary Examiner* — Carlos Azpuru
*Assistant Examiner* — Casey Hagopian
(74) *Attorney, Agent, or Firm* — Morris Manning & Martin, LLP; Tim Tingkang Xia, Esq.

(57) ABSTRACT

A method for growing bone cells. In one aspect, the present invention provides a method for growing bone cells, comprising the steps of (a) anodizing a titanium substrate to form an array of titanium dioxide nanotubes on a surface of the titanium substrate, (b) subjecting the anodized titanium substrate to a radio frequency plasma discharge to chemically modify the array of titanium dioxide nanotubes formed on the surface of the titanium substrate, (c) seeding bone cells onto the surface of the titanium substrate that has an array of titanium dioxide nanotubes thereon after the subjecting step, and (d) incubating the seeded bone cells for a period of time effective for the cells to grow and proliferate.

14 Claims, 8 Drawing Sheets

(56) References Cited

OTHER PUBLICATIONS

Xiaolong Zhu et al., Effects of topography and composition of titanium surface oxides on osteoblast responses, Biomaterials, 25 (18), 2004, 4087-4103.

Michael Simon et al., Corrosion resistance and biocompatibility of a new porous surface for titanium implants, European Journal of Oral Sciences, 2005, 113 (6), 537-545.

Webster, T. J., Increased Osteoblast Adhesion on Nanophase Metals: Ti, Ti6Al4V, and CoCrMo, Biomaterials, 2004, 25, 4731-4739.

Ryo Jimbo et al., Enhanced osseointegration by the chemotactic activity of plasma fibronectin for cellular fibronectin positive cells, Biomaterials, 2007, 28, 3469-3477.

Jamie Harle et al., Initial responses of human osteoblasts to sol-gel modified titanium with hydroxyapatite and titania composition, Acta Biomaterialia, 2006, 2 (5), 547-556.

Lakshmi, B. B. et al., Sol-gel template synthesis of semiconductor oxide micro- and nanostructures, Chem Mater., 1997, 9, 2544-2550.

Miao, Z. et al., Electrochemically induced sol-gel preparation of single-crystalline TiO2 nanowires, Nano Letters, 2002, 2, 7, 717-720.

Gong, D, et al., Titanium oxide nanotube arrays prepared by anodic oxidation, J. Mater. Res., 2001, 16, 12, 3331-3334.

Sutherland, M. S. K. et al., Age-dependent expression of osteoblastic phenotypic markers in normal human osteoblasts cultured long-term in the presence of dexamethasone, Osteoporos. Int., 1995, 5 (5), 335-343.

H. A. Declerq et al., Calcification as an indicator of osteoinductive capacity of biomaterials in osteoblastic cell cultures, Biomaterials, 2005, 26, 4964-4974.

Maria Lurdes Pereira et al., Behaviour of human osteoblastic cells cultured on plasma-sprayed titanium implants in the presence of nicotine, Clinical Oral Implants Research, 2008, 19 (6), 582-589.

Thomas J. Balshi et al., Dental Implants in the Diabetic Patient: A Retrospective Study, Implant Dentistry, 1999, 8, 4, 355-359.

Meyer, U., et al., Basic Reactions of Osteoblasts on Structured Material Surfaces, European Cells and Materials, 2005, 9, 39-49.

Kaiyong Cai et al., Surface functionalized titanium thin films: Zeta-potential, protein adsorption and cell proliferation, Colloids and Surfaces B, 2006, 50 (1), 1-8.

Palin, E. et al., Mimicking the Nanofeatures of Bone Increases Bone-Forming Cell Adhesion and Proliferation, Nanotechnology, 2005, 16, 1828-1835.

M. Chen et al., Cell attachment and biocompatibility of polytetrafluorothylene (PTFE) treated with glow-discharge plasma of mixed ammonia and oxygen, J. Biomater. Sci. Polymer Edn., 2003, 14, 9, 917-935.

G. M. Sipehia et al., Enhanced attachment and growth of human endothelial cells derived from umbilical veins on ammonia plasma modified surfaces of PTFE and ePTFE synthetic vascular graft biomaterials, Biomater. Artif. Cells Immobilization Biotechnol., 1993, 21, 4, 455-468.

\* cited by examiner

| BAP | |
|---|---|
| 405 nm | µU/µl |
| 0.087 | 0 |
| 0.098 | 0.12 |
| 0.104 | 0.24 |
| 0.123 | 0.49 |
| 0.165 | 0.98 |
| 0.252 | 1.95 |
| 0.422 | 3.92 |
| 0.749 | 7.81 |
| 1.333 | 15.63 |
| 2.351 | 31.25 |
| 4 | 62.5 |
| 4 | 125 |
| 4 | 250 |
| 4 | 500 |
| 4 | 1000 |

| | 3 Days | | | 7 days | |
|---|---|---|---|---|---|
| | 405 nm | µU/µl | | 405 nm | µU/µl |
| Control | 1.284±0.08 | | Control | 4 | |
| O₂+N₂ | 3.342±0.299 | | O₂+N₂ | 4 | |
| TiO₂ | 0.926±0.012 | | TiO₂ | 3.805±0.336 | |

ENHANCED BONE CELLS GROWTH AND PROLIFERATION ON TIO2 NANOTUBULAR SUBSTRATES TREATED BY RADIO-FREQUENCY PLASMA DISCHARGE

CROSS-REFERENCE TO RELATED PATENT APPLICATION

This application claims the benefit, pursuant to 35 U.S.C. §119(e), of U.S. provisional patent application Ser. No. 61/317,834, filed Mar. 26, 2010, entitled "Enhanced Bone Cells Growth and Proliferation on $TiO_2$ Nanotubular Substrates Treated by RF Plasma Discharge," by Alexandru S. Biris, which is incorporated herein by reference in its entirety.

Some references, which may include patents, patent applications and various publications, are cited in a reference list and discussed in the description of this invention. The citation and/or discussion of such references is provided merely to clarify the description of the present invention and is not an admission that any such reference is "prior art" to the invention described herein. All references listed, cited and/or discussed in this specification are incorporated herein by reference in their entireties and to the same extent as if each reference was individually incorporated by reference.

FIELD OF THE INVENTION

The present invention relates generally to bone cell growth and proliferation, and more particularly to bone cells growth and proliferation on $TiO_2$ nanotubular substrates treated by radio-frequency plasma discharge.

BACKGROUND

Titania ($TiO_2$) is an implant material that has gained a great deal of focus for improving the bioactivity of traditional orthopedic [1,2]. The valuable mechanical and chemical properties of titanium, such as its light weight, tensile strength, biocompatibility, biological inertness, and its thin indigenous oxide layer of $TiO_2$, make it one of the most commonly used orthopedic material because of its good osseointegration with the adjoining bone tissue [3,4]. Still some problems that are associated with this material used in implantable devices remain to be solved, such as a certain percentage of integration failures into the bone structures [5, 6]. A special attention needs to be given to the morphology of the oxide films that cover the metal implants since the oxide films will represent the interface between the implant and the host biological system. The essential problem with using bio-implants is their degradation and undesirable biochemical activity with biological tissues adjacent to the implanted material. Considerable efforts have been made to improve the surface properties of Ti implants by designing substrates that are more irregular at the nanoscale than conventionally used smooth titanium implants and thus enhancing their ability for osseointegration [7], corrosion resistance [8], and avoidance of infections. More so, these modified surfaces keep the overall valuable characteristics of the native $TiO_2$ substrate such as fracture resistance and biological properties. Increased osteoblast attachment has been shown to take place on surfaces that have been roughened at the nanoscale compared to smooth surfaces [9].

Therefore, a heretofore unaddressed need exists in the art to address the aforementioned deficiencies and inadequacies.

SUMMARY OF THE INVENTION

In one aspect, the present invention provides a method for growing bone cells. In one embodiment, the method includes the steps of (a) anodizing a titanium substrate to form an array of titanium dioxide nanotubes on a surface of the titanium substrate, (b) subjecting the anodized titanium substrate to a radio frequency plasma discharge to chemically modify the array of titanium dioxide nanotubes formed on the surface of the titanium substrate, (c) seeding bone cells onto the surface of the titanium substrate that has an array of titanium dioxide nanotubes thereon after the subjecting step, and (d) incubating the seeded bone cells for a period of time effective for the cells to grow and proliferate.

In one embodiment, as formed after the anodizing step, the titanium dioxide nanotubes in the array are substantially ordered and are oriented substantially vertically on the surface of the titanium substrate.

In one embodiment, the titanium dioxide nanotubes have diameters ranging from about 80 nm to about 107 nm.

In one embodiment, the titanium dioxide nanotubes are about 4 mm in height.

In one embodiment, the plasma discharge comprises an ionized gas selected from the group consisting of oxygen gas, nitrogen gas, a mixture of oxygen gas and nitrogen gas, and helium gas.

In one embodiment, the radio frequency of the plasma discharge is about 13.56 MHz.

In one embodiment, the pressure of the ionized gas is about 150 mTorr.

In one embodiment, in the seeding step, the titanium substrate is immersed in a medium contained in a well.

In one embodiment, the bone cells are seeded at a density of about $1 \times 10^4$ cells per well.

In one embodiment, the incubating step lasts for a period of time about 3 days.

In one embodiment, the incubating step lasts for a period of time about 7 days.

In one embodiment, the method further includes the step of culturing bone cells prior to the seeding step.

In one embodiment, the bone cells are murine calvaria-derived MC3T3-E1 osteoblast-like cells.

In one embodiment, the bone cells are cultured in a container containing a phenol red free alpha-modified minimum essential medium.

In one embodiment, the phenol red free alpha-modified minimum essential medium contains about 10% fetal bovine serum (FBS), and about 1% penicillin and streptomycin, respectively.

In one embodiment, the culturing step is performed at about 37° C.

In another embodiment, the culturing step is performed in an atmosphere containing about 5% carbon dioxide ($CO_2$).

In yet another embodiment, the bone cells are cultured for a period of time about 7 days.

In a further embodiment, the method further includes the step of sub-culturing the bone cells by trypsinization after the culturing step and prior to the seeding step.

In another aspect, the present invention provides an article of manufacture made by the method set forth immediately above.

In another aspect, the present invention provides a method for growing bone cells. In one embodiment, the method includes the steps of: (a) providing a titanium substrate having an array of $TiO_2$ nanotubes formed on a surface thereof; (b) subjecting the substrate to a radio frequency plasma discharge to chemically modify the array of $TiO_2$ nanotubes, (c) seeding bone cells onto the surface of the substrate that has an array of $TiO_2$ nanotubes after the subjecting step, and (d) incubating the seeded bone cells for a period of time effective for the cells to grow and proliferate.

In one embodiment, the radio frequency of the plasma discharge is about 13.56 MHz.

In another embodiment, the plasma discharge comprises an ionized gas selected from the group consisting of oxygen gas, nitrogen gas, a mixture of oxygen gas and nitrogen gas, and helium gas.

In yet another embodiment, the pressure of the ionized gas is about 150 mTorr.

In another aspect, the present invention provides an article of manufacture made by the method set forth immediately above.

In yet another aspect, the present invention provides an article of manufacture, comprising: (a) a titanium substrate having an array of $TiO_2$ nanotubes formed on a surface thereof, and (b) a plurality of bone cells grown on the surface of the substrate that has an array of $TiO_2$ nanotubes, wherein the array of $TiO_2$ nanotubes is chemically modified by a radio frequency plasma discharge.

In a further aspect, the present invention provides a method of implanting a titanium implant to a target of interest. In one embodiment, the method includes the steps of (a) providing a titanium substrate having an array of $TiO_2$ nanotubes formed on a surface thereof, wherein the array of $TiO_2$ nanotubes is chemically modified by a radio frequency plasma discharge, and (b) implanting the titanium substrate into a target of interest as a replacement for a part of that target of interest.

These and other aspects of the present invention will become apparent from the following description of the preferred embodiment taken in conjunction with the following drawings and their captions, although variations and modifications therein may be affected without departing from the spirit and scope of the novel concepts of the disclosure.

BRIEF DESCRIPTION OF THE DRAWINGS

The drawings described below are for illustration purposes only. The drawings are not intended to limit the scope of the present teachings in any way. The patent or application file may contain at least one drawing executed in color. If so, copies of this patent or patent application publication with color drawing(s) will be provided by the Office upon request and payment of the necessary fee.

DETAILED DESCRIPTION

The present invention is more particularly described in the following examples that are intended as illustrative only since numerous modifications and variations therein will be apparent to those skilled in the art. Various embodiments of the invention are now described in detail. Referring to the drawings, FIGS. 1-7, like numbers, if any, indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, if any, the term "atomic force microscope (AFM)" or scanning force microscope (SFM) refers to a very high-resolution type of scanning probe microscope, with demonstrated resolution of fractions of a nanometer, more than 1000 times better than the optical diffraction limit. The term "microscope" in the name of "AFM" is actually a misnomer because it implies looking, while in fact the information is gathered or the action is taken by "feeling" the surface with a mechanical probe. The AFM in general has a microscale cantilever with a tip portion (probe) at its end that is used to scan the specimen surface. The cantilever is typically silicon or silicon nitride with a tip radius of curvature on the order of nanometers. When the tip is brought into proximity of a sample surface, forces between the tip and the sample lead to a deflection of the cantilever according to Hooke's law. The AFM can be utilized in a variety of applications.

As used herein, if any, the term "scanning electron microscope (SEM)" refers to a type of electron microscope that images the sample surface by scanning it with a high-energy beam of electrons in a raster scan pattern. The electrons interact with the atoms that make up the sample producing signals that contain information about the sample's surface topography, composition and other properties such as electrical conductivity.

As used herein, if any, the term "X-ray photoelectron spectroscopy (XPS)" refers to a quantitative spectroscopic technique that measures the elemental composition, empirical formula, chemical state and electronic state of the elements that exist within a material. XPS spectra are obtained by irradiating a material with a beam of X-rays while simultaneously measuring the kinetic energy and number of electrons that escape from the top 1 to 10 nm of the material being analyzed. XPS requires ultra high vacuum (UHV) conditions.

As used herein, if any, the term "Raman spectroscopy" or "Raman technique" refers to an optical technique that probes the specific molecular content of a sample by collecting in-elastically scattered light. As photons propagate through a medium, they undergo both absorptive and scattering events. In absorption, the energy of the photons is completely transferred to the material, allowing either heat transfer (internal conversion) or re-emission phenomena such as fluorescence and phosphorescence to occur. Scattering, however, is normally an in-elastic process, in which the incident photons retain their energy. In Raman scattering, the photons either donate or acquire energy from the medium, on a molecular level. In contrast to fluorescence, where the energy transfers are on the order of the electronic bandgaps, the energy transfers associated with Raman scattering are on the order of the vibrational modes of the molecule. These vibrational modes are molecularly specific, giving every molecule a unique Raman spectral signature.

Raman scattering is a very weak phenomena, and therefore practical measurement of Raman spectra of a medium requires high power excitation laser sources and extremely sensitive detection hardware. Even with these components, the Raman spectra from tissue are masked by the relatively intense tissue auto-fluorescence. After detection, post processing techniques are required to subtract the fluorescent background and enable accurate visualization of the Raman spectra. Raman spectra are plotted as a function of frequency shift in units of wavenumber ($cm^{-1}$). The region of the Raman spectra where most biological molecules have Raman peaks is from 500 to 2000 $cm^{-1}$. In contrast to fluorescence spectra, Raman spectra have sharp spectral features that enable easier identification of the constituent sources of spectral peaks in a complex sample.

As used herein, "nanoscopic-scale," "nanoscopic," "nanometer-scale," "nanoscale," "nanocomposites," "nanoparticles," the "nano-" prefix, and the like generally refers to elements or articles having widths or diameters of less than about 1 µm, preferably less than about 100 nm in some cases. In all embodiments, specified widths can be smallest width (i.e. a width as specified where, at that location, the article can have a larger width in a different dimension), or largest width (i.e. where, at that location, the article's width is no wider than as specified, but can have a length that is greater).

As used herein, "plurality" means two or more.

As used herein, the terms "comprising," "including," "carrying," "having," "containing," "involving," and the like are to be understood to be open-ended, i.e., to mean including but not limited to.

OVERVIEW OF THE INVENTION

Titania ($TiO_2$) is an implant material that has gained a great deal of focus for improving the bioactivity of traditional orthopedic [1, 2]. The valuable mechanical and chemical properties of titanium, such as its light weight, tensile strength, biocompatibility, biological inertness, and its thin indigenous oxide layer of $TiO_2$, make it one of the most commonly used orthopedic material because of its good osseointegration with the adjoining bone tissue [3,4]. Still some problems that are associated with this material used in implantable devices remain to be solved, such as a certain percentage of integration failures into the bone structures [5, 6]. A special attention needs to be given to the morphology of the oxide films that cover the metal implants since the oxide films will represent the interface between the implant and the host biological system. The essential problem with using bio-implants is their degradation and undesirable biochemical activity with biological tissues adjacent to the implanted material. Considerable efforts have been made to improve the surface properties of Ti implants by designing substrates that are more irregular at the nanoscale than conventionally used smooth titanium implants and thus enhancing their ability for osseointegration [7], corrosion resistance [8], and avoidance of infections. More so, these modified surfaces keep the overall valuable characteristics of the native $TiO_2$ substrate such as fracture resistance and biological properties. Increased osteoblast attachment has been shown to take place on surfaces that have been roughened at the nanoscale compared to smooth surfaces [9].

Osteoblastic cells have shown good proliferation on implant surfaces coated with biological molecules [10] and exposed to electrochemical treatments [11]. Many techniques, such as thermal oxidation, anodization, as well as sol-gel application, have been used to minimize corrosion and maximize biocompatibility in Ti implants [12, 13, 14] showing a greater cellular proliferation compared to their untreated control surfaces.

In one embodiment of the present invention, the biological induced responses and the proliferation of mouse osteoblastic cells over $TiO_2$ nanotubular arrays grown over Ti surfaces by electrochemical anodization were studied. These irregularities closely mimic the surface topography of bone, and achieving this similarity is a major goal of implant coating design. It was demonstrated that by exposing the nanotubular arrays to a plasma discharge treatment of various gases ($O_2$, $N_2$, their combination, and He) have significantly enhanced the cellular proliferation as compared to the untreated $TiO_2$ nanotube surfaces. One aspect of the present invention was related to forming superior titania-based implant coatings by adjusting the structural morphology of the $TiO_2$ nano-tubular substrates and introducing chemical modifications onto their surfaces. Earlier studies indicated an accelerated cellular growth on $TiO_2$ nanotube surfaces, but the results presented in this disclosure, further show that besides the structural properties of the surfaces also the chemical modifications induced by the plasma discharge process, significantly improve the cell proliferation over the titania nanotube surfaces [20, 21]. These studies were further supported by examining the alkaline phosphatase activity.

Thus, in one aspect, the present invention provides a method for growing bone cells. In one aspect, the present invention provides a method for growing bone cells, comprising the steps of: (a) anodizing a titanium substrate to form an array of titanium dioxide nanotubes on a surface of the titanium substrate, (b) subjecting the anodized titanium substrate to a radio frequency plasma discharge to chemically modify the array of titanium dioxide nanotubes formed on the surface of the titanium substrate, (c) seeding bone cells onto the surface of the titanium substrate that has an array of titanium dioxide nanotubes thereon after the subjecting step, and (d) incubating the seeded bone cells for a period of time effective for the cells to grow and proliferate.

In one embodiment, as formed after the anodizing step, the titanium dioxide nanotubes in the array are substantially ordered and are oriented substantially vertically on the surface of the titanium substrate.

In one embodiment, the titanium dioxide nanotubes have diameters ranging from about 80 nm to about 107 nm.

In one embodiment, the titanium dioxide nanotubes are about 4 mm in height.

In one embodiment, the plasma discharge comprises an ionized gas selected from the group consisting of oxygen gas, nitrogen gas, a mixture of oxygen gas and nitrogen gas, and helium gas.

In one embodiment, the radio frequency of the plasma discharge is about 13.56 MHz.

In one embodiment, the pressure of the ionized gas is about 150 mTorr.

In one embodiment, in the seeding step, the titanium substrate is immersed in a medium contained in a well.

In one embodiment, the bone cells are seeded at a density of about $1 \times 10^4$ cells per well.

In one embodiment, the incubating step lasts for a period of time about 3 days.

In one embodiment, the incubating step lasts for a period of time about 7 days.

In one embodiment, the method further comprising the step of culturing bone cells prior to the seeding step.

In one embodiment, the bone cells are murine calvaria-derived MC3T3-E1 osteoblast-like cells.

In one embodiment, the bone cells are cultured in a container containing a phenol red free alpha-modified minimum essential medium.

In one embodiment, the phenol red free alpha-modified minimum essential medium contains about 10% fetal bovine serum (FBS), and about 1% penicillin and streptomycin, respectively.

In one embodiment, the culturing step is performed at about 37° C.

In another embodiment, the culturing step is performed in an atmosphere containing about 5% carbon dioxide ($CO_2$).

In yet another embodiment, the bone cells are cultured for a period of time about 7 days.

In a further embodiment, the method further comprising the step of sub-culturing the bone cells by trypsinization after the culturing step and prior to the seeding step.

In another aspect, the present invention provides an article of manufacture made by the method set forth immediately above.

In another aspect, the present invention provides a method for growing bone cells, comprising the steps of: (a) providing a titanium substrate having an array of $TiO_2$ nanotubes formed on a surface thereof, (b) subjecting the substrate to a radio frequency plasma discharge to chemically modify the array of $TiO_2$ nanotubes, (c) seeding bone cells onto the surface of the substrate that has an array of $TiO_2$ nanotubes after the subjecting step, and (d) incubating the seeded bone cells for a period of time effective for the cells to grow and proliferate.

In one embodiment, the radio frequency of the plasma discharge is about 13.56 MHz.

In another embodiment, the plasma discharge comprises an ionized gas selected from the group consisting of oxygen gas, nitrogen gas, a mixture of oxygen gas and nitrogen gas, and helium gas.

In yet another embodiment, the pressure of the ionized gas is about 150 mTorr.

In another aspect, the present invention provides an article of manufacture made by the method set forth immediately above.

In yet another aspect, the present invention provides an article of manufacture, comprising: (a) a titanium substrate having an array of $TiO_2$ nanotubes formed on a surface thereof, and (b) a plurality of bone cells grown on the surface of the substrate that has an array of $TiO_2$ nanotubes, wherein the array of $TiO_2$ nanotubes is chemically modified by a radio frequency plasma discharge.

In a further aspect, the present invention provides a method of implanting a titanium implant to a target of interest, comprising the steps of (a) providing a titanium substrate having an array of $TiO_2$ nanotubes formed on a surface thereof, wherein the array of $TiO_2$ nanotubes is chemically modified by a radio frequency plasma discharge, and (b) implanting the titanium substrate into a target of interest as a replacement for a part of that target of interest.

Additional details are set forth below.

EXAMPLES

Aspects of the present teachings may be further understood in light of the following examples, which should not be construed as limiting the scope of the present teachings in any way.

Example 1

This example describes the experimental procedures according to one embodiment of the present invention.

Figure 1A:
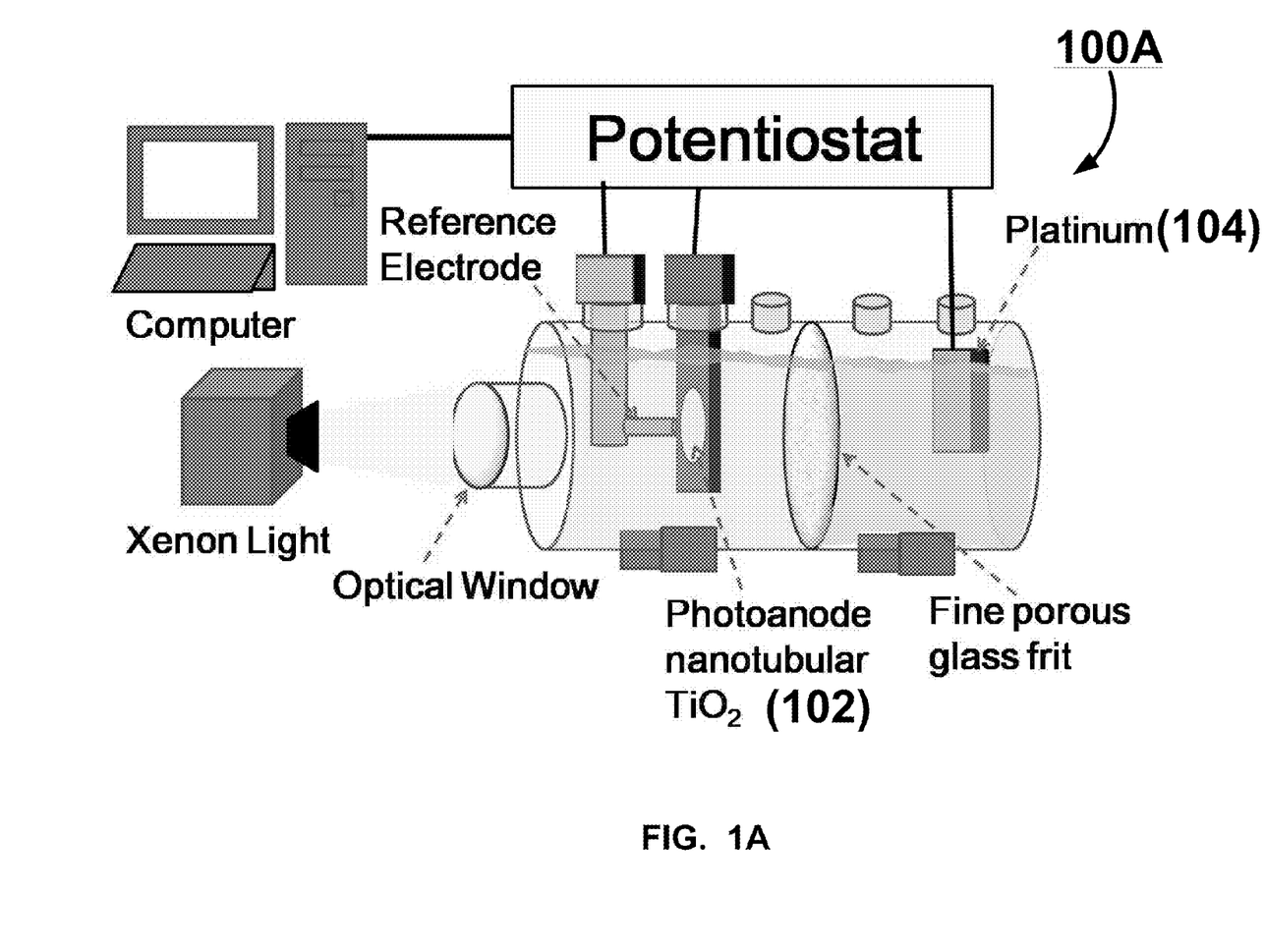
FIG. 1 shows the schematics of the experimental setups of the anodizing process used to synthesize the $TiO_2$ nanotubular arrays (A) and to plasma treat them under various gas conditions (B) according to one embodiment of the present invention.

Electrochemical Synthesis of $TiO_2$ Nanotubular Arrays:

In one embodiment of the present invention, $TiO_2$ nanotubular and nanocrystalline structures were synthesized on a titanium metal foil support (99.9% pure, 0.5 mm thick) using a conventional anodization process (95 wt. % ethylene glycol+5 wt. % $NH_4F$; 20 V, 1 A, 1 hour) (FIG. 1A). A two-electrode configuration 100A was used for anodization. A titanium substrate served as an anode 102. A platinum electrode (thickness: 1 mm; area: 3.75 $cm^2$) served as a cathode 104. The distance between the two electrodes 102, 104 was kept at 4.5 cm in all experiments. Anodization was carried out at a constant potential of 20 V using a DC voltage supply (Agilent, E3640A). The anodization current was monitored continuously using a digital multimeter (METEX, MXD 4600 A). After an initial increase—decrease transient, the current reached a steady-state value. The anodized samples were washed with distilled water to remove the occluded ions from the anodized solutions and dried in an air-oven.

Figure 1B:
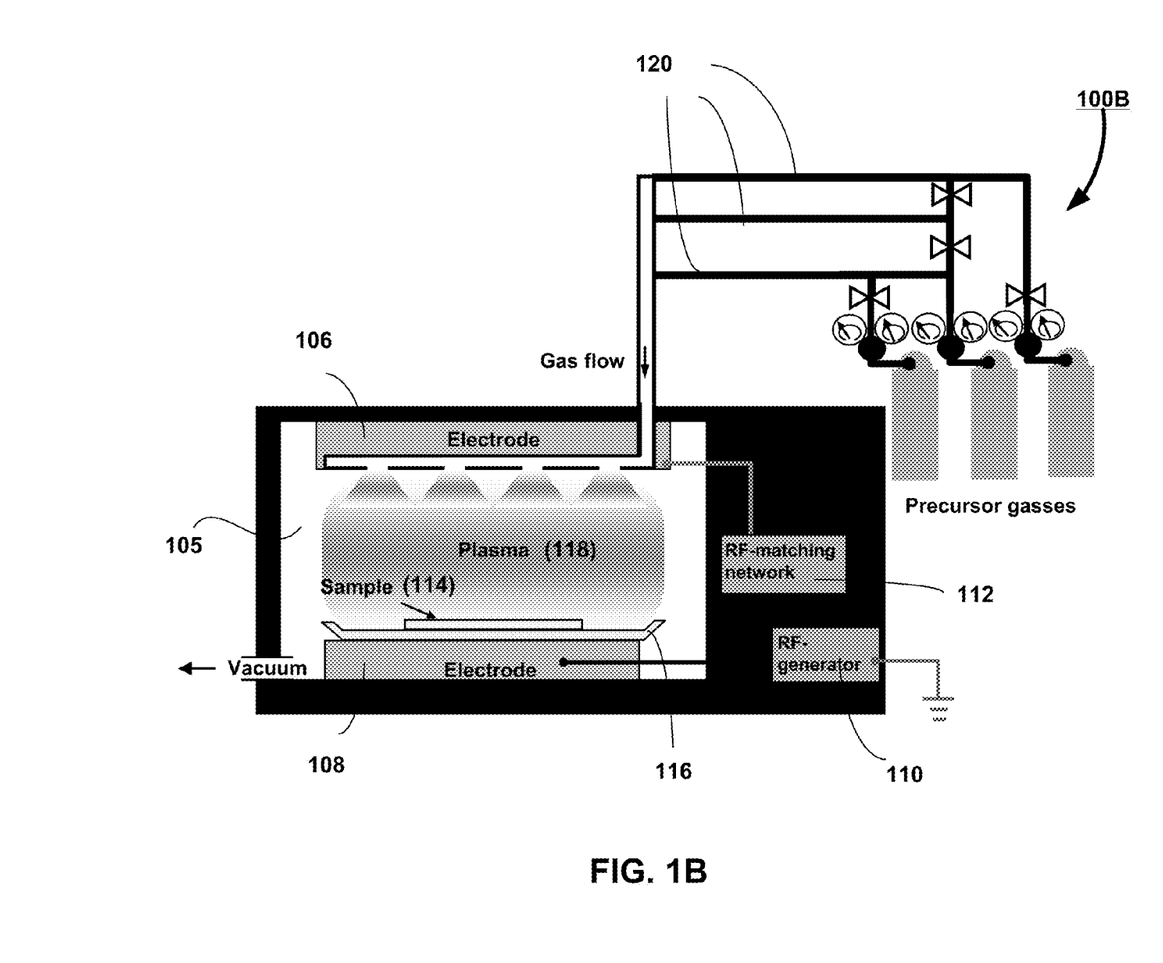

Plasma Surface Treatment:

Prior to thermal treatments, the $TiO_2$ films were plasma treated following anodization and subsequent air-drying. The plasma reactor 100B has a chamber 105 and two parallel aluminum electrodes 106 and 108, which are positioned on opposite, inner surfaces of chamber 105 respectively, as shown in FIG. 1B. The plasma 118 was generated between the electrodes 106 and 108 using a 13.56 MHz RF power supply 110 (MCS Plasma Systems Model HF-3) with an impedance matching network 112. Sample 114 was placed in a ceramic boat 116, which itself was positioned between the electrodes 106 and 108. The reactor 100B further has a unique gas flow design where gas was dispersed into the chamber 105 using a series of inlets 120 from the top electrode 106. Nitrogen was used as processing gas with an operating pressure of 150 mTorr. The sample or samples were routinely exposed to argon "cleaning" plasma for five minutes followed by nitrogen plasma for one hour.

Primary Cell Cultures:

The murine calvaria-derived MC3T3-E1 osteoblast-like cells were obtained from the American Type Culture Collection (ATCC) and maintained using established procedures. Cell cultures exhibiting exponential growth phase were normally grown in 75 $cm^2$ flasks (density of $10^6$) with phenol red free alpha-modified minimum essential medium containing 10% fetal bovine serum (FBS), 1% penicillin (500 units/ml) and streptomycin (500 units/ml) at 37° C. in 5% $CO_2$ atmosphere 7 days prior to seeding onto each coating, then subcultured by trypsinization for further experiments. The cells were kept in aseptic conditions and the media was changed every 2-3 days.

Cell Incubation at Different Conditions:

Cells were seeded at a density of $1 \times 10^4$ cells/well in 24 well plates into five different surface treatments in replicate experiments; $TiO_2$, $TiO_2$ plasma treated plates with ($O_2$, $N_2$, $O_2+N_2$, He) and control samples on regular plastic plates. The cells were incubated for 3 and 7 days prior to cell proliferation analysis and the medium was replaced with fresh solution every three days. All treatments, including the control, were performed in triplicate samples.

Cell Assessment with Light Microscopy:

For microscopic studies, cells were grown under the same conditions as with their incubation. Following the incubation methods above, the cells were washed thoroughly with 10 mM phosphate buffered saline (PBS, pH 7.4) three times and fixed with 10% formaldehyde solution for 10 minutes, washed three times with PBS and stained with ethedium bromide-acridine orange fluorescent dye. The cells were monitored with UV light by light transmission microscopy using an Olympus BX 51 microscope.

Cellular Proliferation Analysis:

Cell proliferation was performed by the well known Trypan blue assay [22]. First, the cells were cultured as described above for 7 days under various conditions. The cells were then dissociated from the bottom of the plates by trypsinization and transferred to 1.5 ml eppendorf tubes. The solutions, including the detached cells, were centrifuged at 1000 rpm for 10 minutes and removed by suction. The detached cells on each sample were stained with 100 μL of 1× Trypan blue dye with 1× PBS trypan blue dye agent (Invitrogen) at room temperature for 5 minutes. 10 μL of the stained cells were transferred to a hematocytometer and counted using an optical microscope.

Activity of Alkaline Phosphatase (ALP):

MC3T3-E1 cells were inoculated into 24-well plates with varying substrates (plastic control, non-plasma treated titania and $O_2+N_2$ plasma treated titania) at a density of $10^4$ cells/dish and cultured under the same conditions for 3 and 7 days in triplicate samples. ALP activity was examined using the TRACP & ALP double-stain kit (Takara cat #MK301) according to the manufacturer's protocol and the absorbance of each sample at 405 nm was measured with a microplate reader.

Raman Spectroscopy:

Raman spectra of all $TiO_2$ films were collected using a LabRam Micro-Raman Spectrometer (Horiba Jobin-Yvon HR800 UV) equipped with an optical microscope and a 100× objective lens for a total magnification 1000×. An argon-ion (524.5 nm) or helium-neon (632.8 nm) laser was used for laser excitation of the Raman signal with appropriate holographic notch filters for eliminating the laser line after excitation. The laser power at the sample was of 20 mW, and the 1/e laser spot size was about 2 μm at the sample. The slit width of the spectrometer was typically set at 700 μm. An 1800 grooves/mm grating was used which resulted in a spectral resolution of about 1.5 $cm^{-1}$.

Statistical Analysis:

The data were analyzed by one-way analysis of variance (1-way ANOVA) at the level of $p<0.05$.

Example 2

This example describes the experimental results obtained by utilizing the exemplary processes set forth in Example 1, according to one embodiment of the present invention.

$TiO_2$ Synthesis and Characterization

Figure 2:
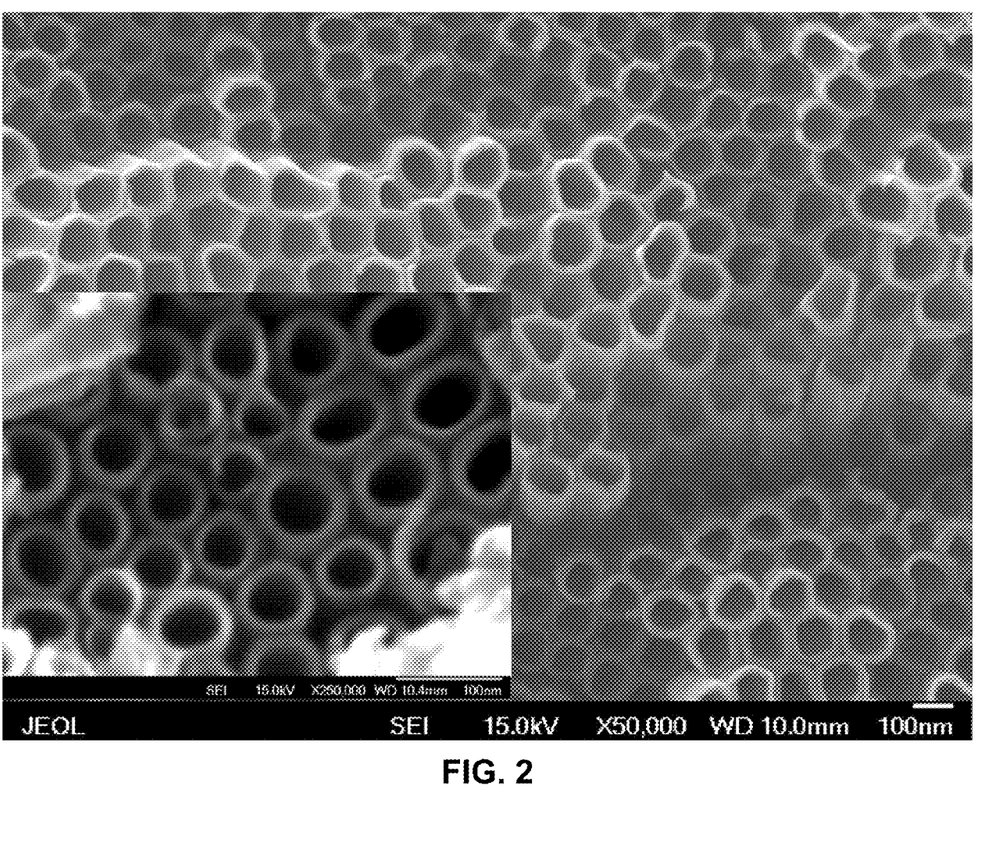
FIG. 2 shows the scanning electron microscropy (SEM) image of the $TiO_2$ nanotube arrays used for studying the proliferation of the osteoblastic cells according to one embodiment of the present invention.
Figure 3:
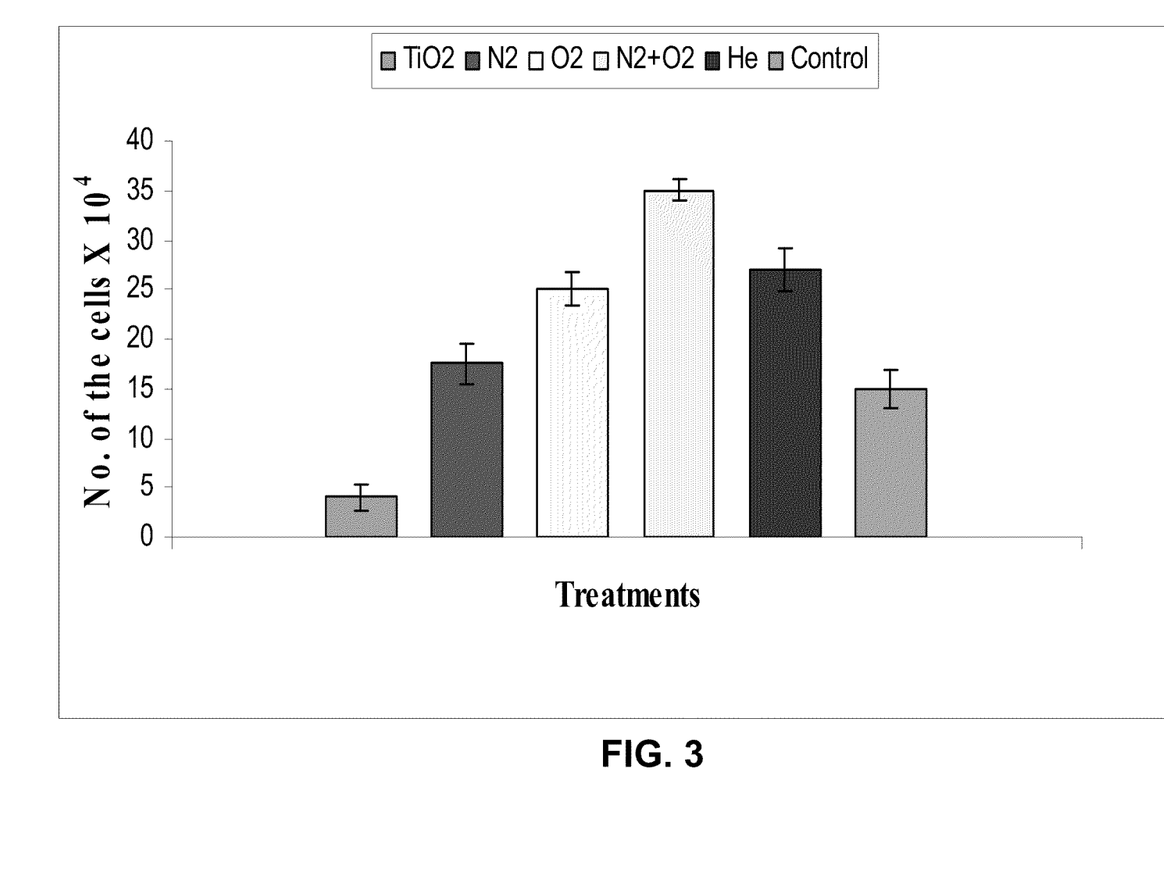
FIG. 3 shows the cell proliferation test results, according to one embodiment of the present invention, the same data as shown in FIG. 6. The cells were plated in a density of $10^4$/well and incubated for 7 days, in 37 C., 5% $CO_2$ in humidified incubator. The growing medium was changed every 2-3 hours.

The $TiO_2$ arrays were produced using an anodization process and a corresponding SEM image is shown in FIG. 2. It can be observed a high uniformity in the diameter of the $TiO_2$ nanotubes which ranged between 80 to 107 nm. The height of the nanotubes was of 4 μm±10%.

Cellular Proliferation of Plasma Treated Titania Arrays

The effect of the plasma treatment on the proliferation of MC3T3-E1 cells grown on $TiO_2$ plates was investigated and was compared with the control untreated samples. The growth ratios of the cells on the samples used in the cell proliferation assays are shown below in FIG. 3. The initial ratio of osteoblast cells growth on untreated samples showed a significantly lower value than in the treated samples. At the end of this testing time (i.e. 7 days), the growth ratio on the gas discharge plasma treated titania arrays ($O_2+N_2$) is statistically greater ($35 \times 10^4$ cells/well) than the untreated samples ($4 \times 10^4$ cells/well) and the control ($15 \times 10^4$ cells/well).

Figure 4:
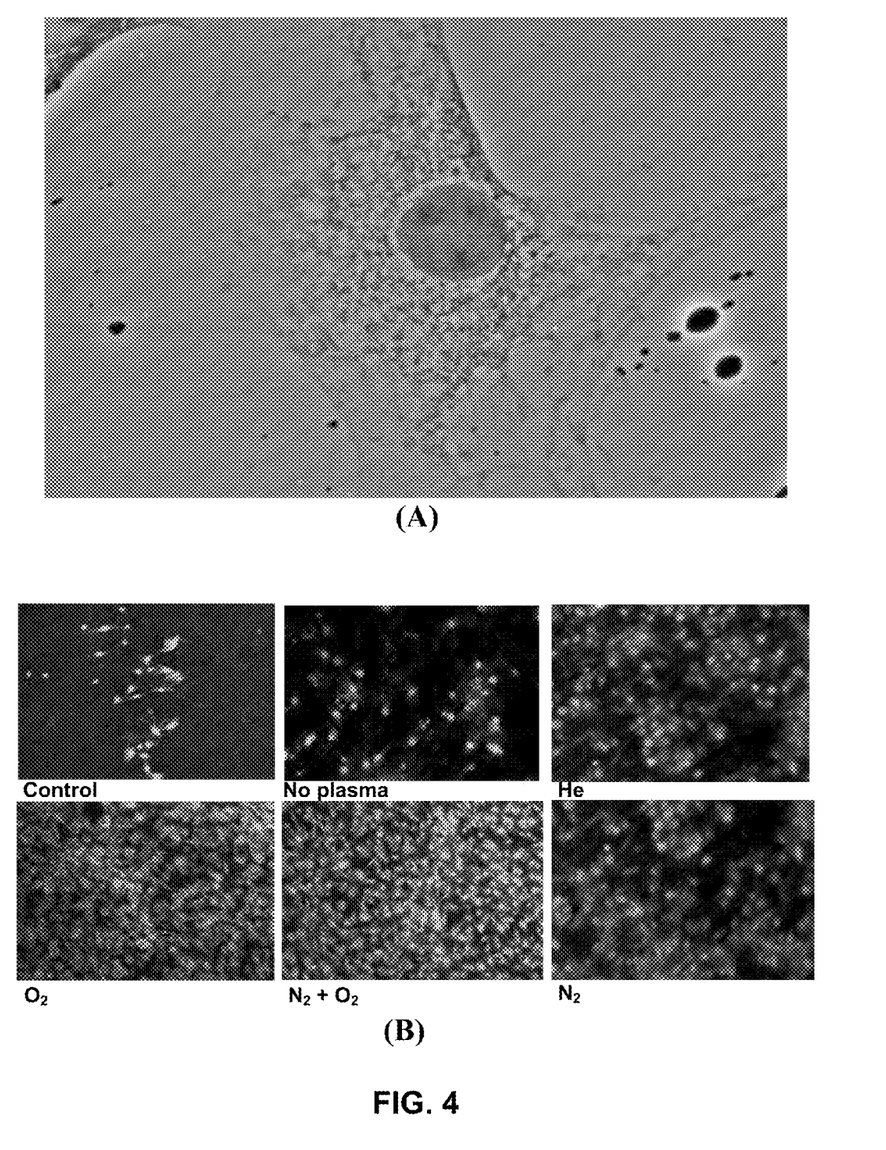
FIG. 4 shows a representative photomicrograph of cultured osteoblastic cells (A) on plasma treated titanium plates compared to the untreated plates and control (B), according to one embodiment of the present invention. The cells were incubated for 7 days, stained with ethedium bromide and the images of the cells were captured via light transmission microscopy (Olympus BX51), using fluorescein isothiocyanate (FITC).
Figure 5:
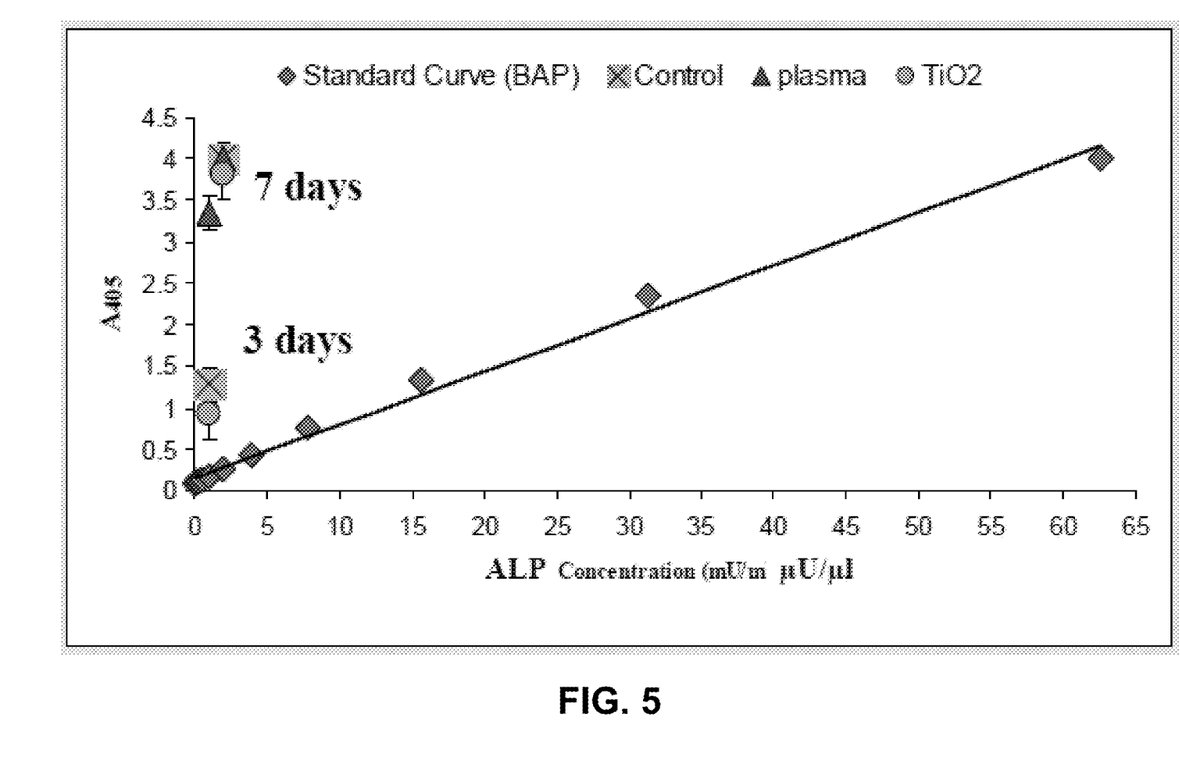
FIG. 5 shows the effect of $O_2$ plus $N_2$ plasma spray on the alkaline phosphatase (ALP) activity of the osteoblasts according to one embodiment of the present invention. Results are shown as mean±standard deviation of triplicate experiments. Bone ALP from TAKARA BIO was used as a positive control.
Figure 6:
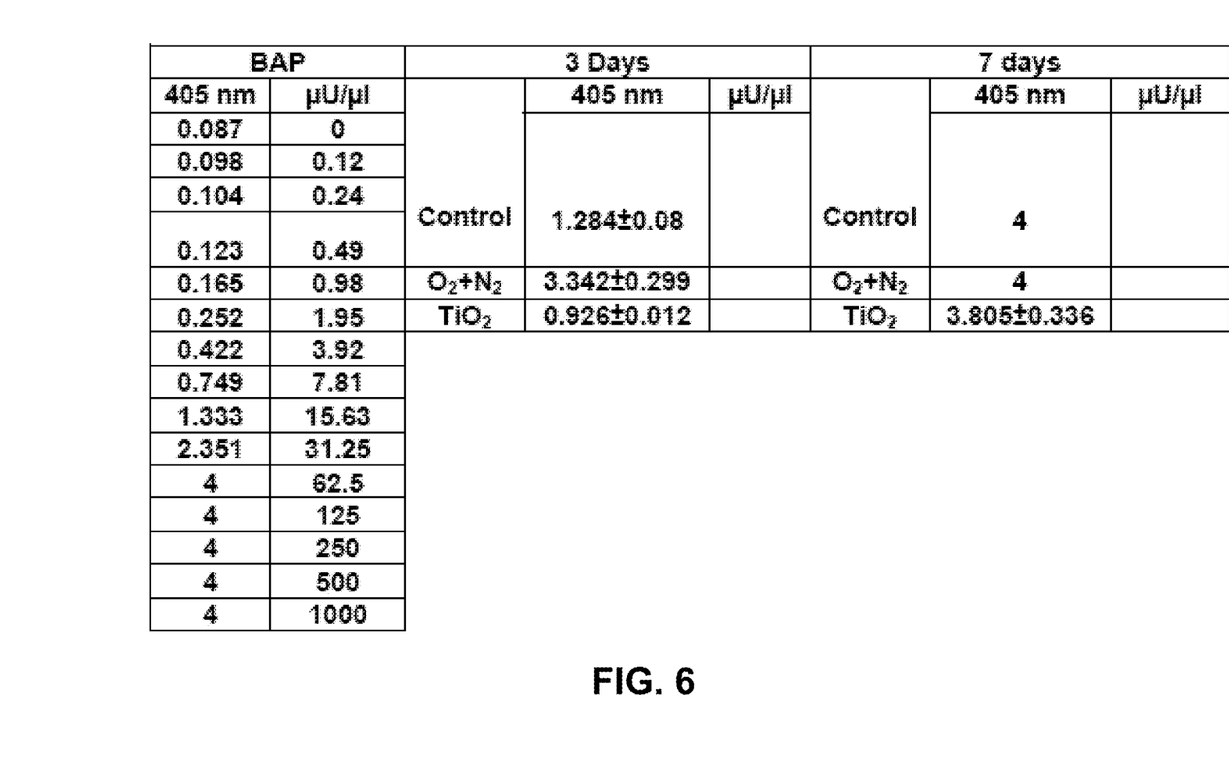
FIG. 6 shows a table that summarizes ALP activity assays at 3 days and 7 days incubation on plastic (as a control), $TiO_2$, and $TiO_2$ plasma-treated plates, according to one embodiment of the present invention. The experiments were performed in triplicate samples and presented as mean values±standard deviation.

The assessment of osteoblast cellular proliferation over the various $TiO_2$ nanotubular arrays using optical microscopy is shown in FIG. 4. For this study, the cells were treated with ethedium bromide-acridine orange fluorescent dye and were visualized under UV radiation. The results indicate clearly that that plasma treated surfaces induced a significantly higher cellular proliferation, which indicated their better biocompatibility towards that bone cells used in this study.

Effect of Plasma Treatment on the ALP Activity

Osteoblast proliferation and differentiation is an essential aspect of bone formation and remodeling, since the orientation and morphology of these cellular matrices will determine final bone properties. Effects of the plasma spray on osteoblast differentiation were investigated using an ALP activity assay; this protein provides an early marker for osteoblast proliferation and differentiation. ALP activity is one of the early phenotypic markers expressed by osteoblast growth [15]. ALP activity measurements bear crucial importance when examining possible bone diseases since ALP is essential for the process of bone mineralization whereby calcium and phosphorus minerals are being deposited and produced. ALP is disseminated in various tissues such as liver and small intestine, and it is produced by the bone-forming cells-osteoblasts. Most importantly, osteogenesis is an important physiological phenomenon that is influenced by the modification of the ALP enzyme levels in tissues [16].

Most of the osteoblastic markers such as ALP are down regulated during proliferation, and they reach their maximum levels after cellular confluence. Previous work has shown that plasma deposition onto structured surfaces led to a positive stimulation of viability and ALP activity in the osteoblastic cells [17]. Osseointegration and avoidance of infection is essential for the success of the implant [18], and understanding the complex interaction between the cells and these engineered new substrates is needed in order to design optimal coatings for long-term implant materials [19].

The results (FIGS. 5 and 6) suggested that the plasma treatment exhibited complex effects on the proliferation of osteoblasts, which might be caused by the different differentiation states of the cells under varying conditions. Upon treatment with $O_2+N_2$ plasma discharge, osteoblastic proliferation and differentiation were significantly enhanced. In the first 3 days, a maximum difference was observed in the ALP activities produced from the $O_2+N_2$ treated samples and the control. Also, the cells grown on the untreated $TiO_2$ arrays only showed a slight change in the ALP compared to the control. On day 7, the ALP activity of the cells cultured on all plate types (plasma treated $TiO_2$, $TiO_2$ arrays untreated, and plastic control) obviously increased and reached the same level as compared with the $O_2+N_2$ treated samples on day 3. It may be concluded that plasma spray enhances the ALP activity of primary osteoblasts in a time dependent manner.

One aspect of the present invention relates to exploring the potential for plasma treated $TiO_2$ surfaces to enhance osteoblastic proliferation and differentiation rates in vitro and to evaluate the effects of these changes to the tissue-implant interface. The proliferation rates of bone cells were compared. Then the most affecting surface ($O_2+N_2$ plasma treated) was characterized in relation to the other surfaces for its responsiveness to the culture conditions by comparing the proliferation rates among samples of cells grown on the various conditions at 7 days and evaluating the ALP enzyme level of these samples at 3 and 7 days. A key finding was that significantly higher proliferation rates were shown after 3 days for the bone cells grown on the $N_2+O_2$ plasma treated $TiO_2$ surface. Additionally, higher levels of ALP were shown in the same samples after 3 days, confirming the enhancement of osteoblastic proliferation.

Plasma treatment not only roughens the surface of titanium dioxide, it also introduces nitrogen and/or oxygen functional groups, depending on the type of plasma used. This provides a surface with chemical characteristics conducive to osteoblast growth. Plasma treated $TiO_2$-based nanotubular systems have gained a great deal of attention in recent years for their ability to modify the biological behavior of titanium implants. Plasma-coated titanium surfaces are provided according to the present invention for their ability to induce the proliferation of osteoblastic cells under standardized conditions.

Plasma treatment has been known as one of the most versatile techniques in surface modification. Plasma surface modification uses the active species of plasma such as radicals, ions and electrons to alter surface chemistry of materials. The collision of these energetic active species with the surface results in transferring of their energy to lattice atoms. As a result, some of the substrate bonds break, making the surface more reactive. Depending upon the type of precursor gas used to generate the plasma, certain new functional groups can be grafted on the surface. Thus, plasma surface modification can be used to induce a specific surface chemistry without changing the bulk properties of the materials. Surface chemistry can be tailored by varying the different operational parameters involved in the process.

Figure 7:
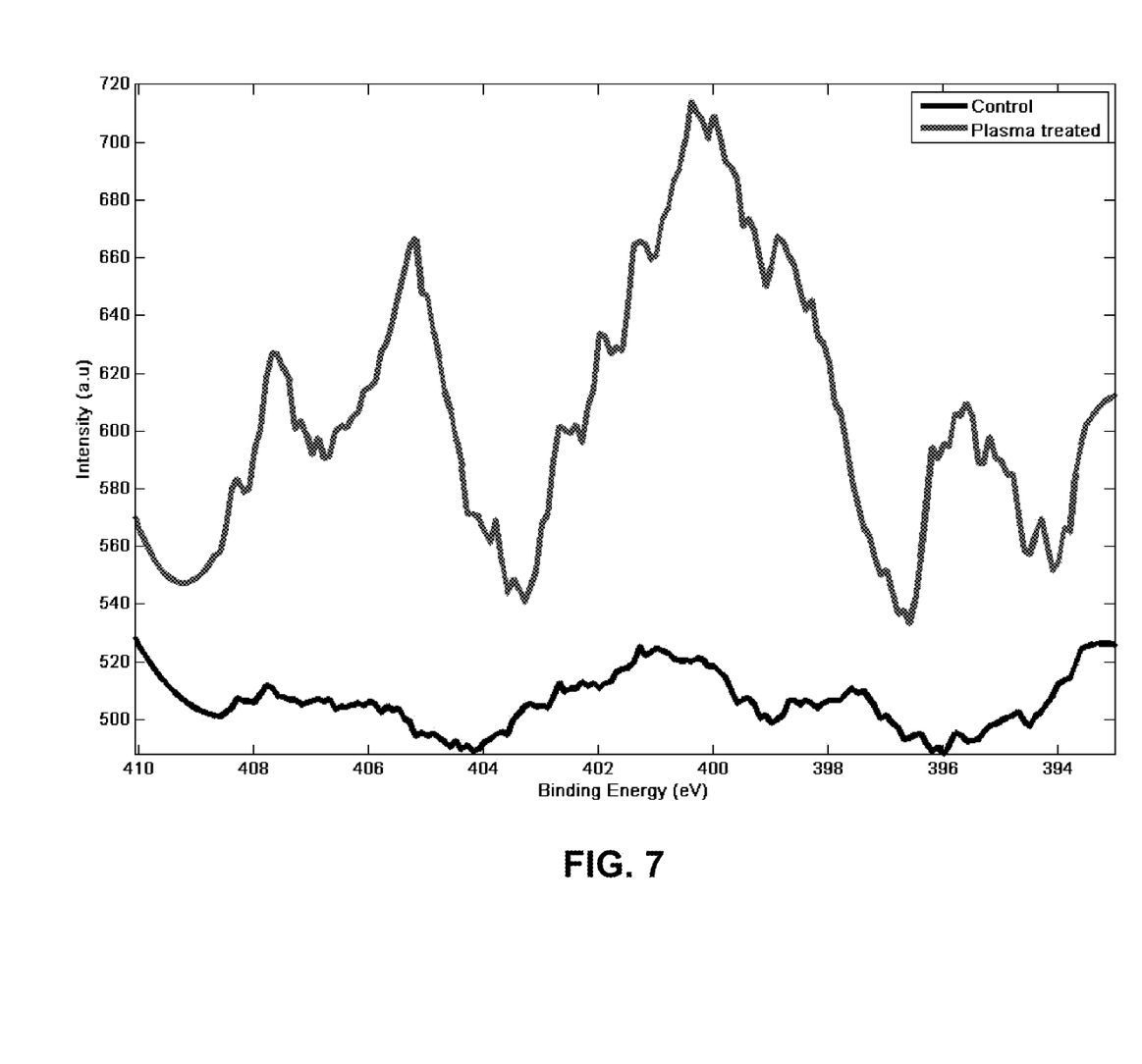
FIG. 7 shows the peak fitted narrow scan X-ray photoelectron spectroscopy (XPS) spectrum of N 1s core-level in (a) Control and, (b) Nitrogen-Plasma treated $TiO_2$ photoanodes, according to one embodiment of the present invention.

XPS analysis of nitrogen plasma treated titania showed that the N-concentration, calculated as a percentage of total anions, increased from 0.24 to 1.21 atomic % after plasma treatment. The significant increase in N concentration after plasma treatment suggests the introduction of N in the lattice structure either as a substitutional dopant for O, or as an interstitial dopant. XPS analysis, presented in FIG. 7, showed an increase in nitrogen concentration on the surface as shown by an observed peak at 396 eV, indicative of substitutional doping of N.

It is noted that nitrogen and ammonia plasma treatments have been shown to introduce amine groups and enhance cell growth on biomaterial surfaces [23,24]. It was shown that a plasma of $O_2+NH_3$ was more conducive for cell growth than plasma of $O_2$ or $NH_3$ alone [23]. The surfaces treated with $O_2+NH_3$ showed greater fibrinogen adsorption resulting in enhanced cell growth.

Both oxygen and nitrogen plasma treated surfaces provided by various embodiments of the present invention exhibited enhanced biocompatibility as compared to untreated titania surface. This is primarily due to formation of nitrogen and oxygen based functional groups which promote cell growth and adhesion. Plasma treatment also caused increase in surface energy which further promotes cell adhesion. However the best results were obtained by a combination of oxygen and nitrogen plasma.

Helium plasma does not result in introduction of any chemical species directly. However, a multitude of prolonged post plasma reactions can introduce various functional groups. Free radicals formed at or below the surface during helium plasma treated have been found to be stable for long durations. When the helium plasma treated surface is exposed to ambient atmosphere, the free radicals on the surface interact with oxygen and nitrogen to form functionalities similar to oxygen and nitrogen plasma treated surfaces. This explains the significant higher cell growth on helium plasma treated surfaces.

Example 3

In one embodiment, the present invention provides a method of implanting a titanium implant to a target of interest. The method includes the steps of (a) providing a titanium substrate having an array of $TiO_2$ nanotubes formed on a surface thereof, wherein the array of $TiO_2$ nanotubes is chemically modified by a radio frequency plasma discharge, according to various embodiments of the present invention and (b) implanting the titanium substrate into a target of interest as a replacement for a part of that target of interest. The target of interest can be, for example, a tooth, a hip, or a knee of a human being or an animal.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1] Seunghan Oh, Chiara Daraio, Li-Han Chen, Thomas R. Pisanic, Rita R. Finones, Sungho Jin; Significantly accelerated osteoblast cell growth on aligned TiO2 nanotubes. Journal of Biomedical Materials Research.

[2] Satomi K, Alagawa Y, Nikai H, Tsuru H. Bone-implant interface structures after nontapping and tapping insertion of screw-type titanium alloy endosseous implants. J Prosthet Dent 1988:59: 339-342.

[3] Linder L, Carlsson A, Marsal L, Bjursten L M, Branemark P I (1988) Clinical aspects of osseointegration in joint replacement. J Bone Joint Surg 70(B):550-555.12.

[4] Puleo D A, Holleran L A, Doremus R H, Bizios R (1991) Osteoblast response to orthopedic implant materials in vivo. J Biomed Mater Res A 25:711-723.

[5] Pinke, P., Zitnansky, M., Caplovic, L., Réger, M.: Biocompatible titanium alloys, First Hungarian Conference on Biomechanics, Budapest, Jun. 11-12, 2004, ISBN 963 420 799 5, pp. 374-382.

[6] Dalby M J, Di Silvio L, Harper E J, Bonfield W. Initial interaction of osteoblasts with the surface of a hydroxyapatite-poly(methylmethacrylate) cement. Biomaterials 2001; 22:1739-1747

[7] Xiaolong Zhu, Jun Chen, Lutz Scheideler, Rudolf Reichl and Juergen Geis-Gerstorfer, Effects of topography and composition of titanium surface oxides on osteoblast responses. Biomaterials, 25(18), 2004, P. 4087-4103.,

[8]. Michael Simon, Christelle Lagneau, José Moreno, Michele Lissac, Francis Dalard, Brigitte Grosgogeat, Corrosion resistance and biocompatibility of a new porous surface for titanium implants, European Journal of Oral Sciences, 113 (6), P. 537-545

[9] Webster T J, Ejiofor J U (2004) Increased Osteoblast Adhesion on Nanophase Metals: Ti, Ti6A14V, and CoCrMo. Biomaterials 25: 4731-4739.

[10] Ryo Jimbo, Takashi Sawase, Yasuaki Shibata, Kazunari Hirata, Yoshitaka Hishikawa, Yasuhiro Tanaka, Kazuhisa Bessho, Tohru Ikeda, Mitsuru Atsuta, Enhanced osseointegration by the chemotactic activity of plasma fibronectin for cellular fibronectin positive cells. Biomaterials 28 (2007) 3469-3477

[11] Jamie Harle, Hae-Won Kim, Nicky Mordan, Jonathan C. Knowles, Vehid Salih, Initial responses of human osteoblasts to sol-gel modified titanium with hydroxyapatite and titania composition

[12] Lakshmi B B, Patrissi C J, Martin C R. Sol-gel template synthesis of semiconductor oxide micro- and nanostructures. Chem Mater 1997; 9:2544-2550,

[13] Miao Z, Xu D, Ouyang J, Guo G, Zhao X, Tang Y. Electrochemically induced sol-gel preparation of single-crystalline TiO2 nanowires. Nano Lett 2002; 2:717-720,

[14] Gong D, Grimes C A, Varghese O K, Hu W, Singh R S, Chen Z, Dickey E C. Titanium oxide nanotube arrays prepared by anodic oxidation. J Mater Res 2001; 16:3331-3334.

[15] Sutherland M S, Rao L G, Muzaffar S A, Wylie J N, Wong M M, McBroom R J, Murray T M. Age-dependent expression of osteoblastic phenotypic markers in normal human osteoblasts cultured long-term in the presence of dexamethasone. Osteoporos Int. 1995; 5(5):335-43

[16] H.a. declerq, r.m.h. verbeeck, l.i.f.j.m. de ridder, e.h. schacht and m.j Calcification as an indicator of osteoinductive capacity of biomaterials in osteoblastic cell cultures. biomaterials 26 (2005), p. 4964.

[17] Maria Lurdes Pereira, João Costa Carvalho, Fernando Peres, Manuel Gutierres and Maria Helena Fernandes. Behaviour of human osteoblastic cells cultured on plasma-sprayed titanium implants in the presence of nicotine. Clinical Oral Implants Research. 19 (6), P. 582-589. 2008.

[18] Thomas J. Balshi, and Glenn J. Wolfinger Dental Implants in the Diabetic Patient—A Retrospective Study, Implant Dentistry/Volume 8, Number 4-1999. Page 355.

[19] Meyer U, Buchter A, Wiesmann H P, Joos U, Jones D B (2005) Basic Reactions of Osteoblasts on Structured Material Surfaces. European Cells and Materials 9: 39-49.

[20] Kaiyong Cai, Marion Frant, Jörg Bossert, Gerhard Hildebrand, Klaus Liefeith and Klaus D. Jandt. Surface functionalized titanium thin films: Zeta-potential, protein adsorption and cell proliferation. Colloids and Surfaces B: Biointerfaces 50(1), 2006, P. 1-8.

[21] Palin E, Liu H, Webster T (2005) Mimicking the Nanofeatures of Bone Increases Bone-Forming Cell Adhesion and Proliferation. Nanotechnology 16: 1828-1835.

[22] Seunghan Oh, Chiara Daraio, Li-Han Chen, Thomas R. Pisanic, Rita R. Finones, Sungho Jin. Significantly accelerated osteoblast cell growth on aligned TiO2 nanotubes. Journal of Biomedical Materials Research Part A DOI 10.1002/jbm.a.

[23] M. Chen, P. Zamora, P. Som, L. Pena, and S. Osaki, "Cell attachment and biocompatibility of polytetrafluorothylene (PTFE) treated with glow-discharge plasma of mixed ammonia and oxygen," J. Biomater. Sci. Polymer Edn., vol. 14, no. 9, pp. 917-935, 2003.

[24] G. M. Sipehia, M. Barbarosie, and C. Wu, "Enhanced attachment and growth of human endothelial cells derived from umbilical veins on ammonia plasma modified surfaces of PTFE and ePTFE synthetic vascular graft biomaterials," Biomater Artif Cells Immobilization Biotechnol., vol. 21, no. 4, pp. 455-468, 1993.

What is claimed is:

1. A method for growing bone cells, comprising the steps of:
   (a) anodizing a titanium substrate to form an array of titanium dioxide nanotubes on a surface of the titanium substrate;
   (b) subjecting the anodized titanium substrate to a radio frequency plasma discharge to chemically modify the array of titanium dioxide nanotubes formed on the surface of the titanium substrate;
   (c) seeding bone cells onto the surface of the titanium substrate that has an array of titanium dioxide nanotubes thereon after the subjecting step; and
   (d) incubating the seeded bone cells for a period of time effective for the cells to grow and proliferate,
      wherein the plasma discharge comprises an ionized gas selected from the group consisting of oxygen gas, nitrogen gas, a mixture of oxygen gas and nitrogen gas, and helium gas; and wherein the radio frequency of the plasma discharge is about 13.56 MHz.

2. The method of claim 1, wherein, as formed after the anodizing step, the titanium dioxide nanotubes in the array are ordered and are oriented vertically on the surface of the titanium substrate.

3. The method of claim 2, wherein the titanium dioxide nanotubes have diameters ranging from about 80 nm to about 107 nm.

4. The method of claim 3, wherein the titanium dioxide nanotubes are about 4 mm in height.

5. The method of claim 1, wherein the ionized gas has a pressure of about 150 mTorr.

6. A method for growing bone cells, comprising the steps of:
   (a) anodizing a titanium substrate to form an array of titanium dioxide nanotubes on a surface of the titanium substrate;
   (b) subjecting the anodized titanium substrate to a radio frequency plasma discharge to chemically modify the array of titanium dioxide nanotubes formed on the surface of the titanium substrate;
   (c) seeding bone cells onto the surface of the titanium substrate that has an array of titanium dioxide nanotubes thereon after the subjecting step; and
   (d) incubating the seeded bone cells for a period of time effective for the cells to grow and proliferate,
      wherein, in the seeding step, the titanium substrate is immersed in a medium contained in a well;
      wherein the bone cells are seeded at a density of about $1 \times 10^4$ cells per well; and
      wherein the incubating step lasts for a period of time about 7 days.

7. A method for growing bone cells, comprising the steps of:
   (a) anodizing a titanium substrate to form an array of titanium dioxide nanotubes on a surface of the titanium substrate;
   (b) subjecting the anodized titanium substrate to a radio frequency plasma discharge to chemically modify the array of titanium dioxide nanotubes formed on the surface of the titanium substrate;
   (c) culturing bone cells;
   (d) seeding the cultured bone cells onto the surface of the titanium substrate that has an array of titanium dioxide nanotubes thereon after the subjecting step; and
   (e) incubating the seeded bone cells for a period of time effective for the cells to grow and proliferate,
      wherein the bone cells are cultured for a period of time about 7 days.

8. The method of claim 7, wherein the bone cells are murine calvaria-derived MC3T3-E1 osteoblast-like cells.

9. The method of claim 7, wherein the bone cells are cultured in a container containing a phenol red free alpha-modified minimum essential medium.

10. The method of claim 9, wherein the phenol red free alpha-modified minimum essential medium contains about 10% fetal bovine serum (FBS), and about 1% penicillin and streptomycin, respectively.

11. The method of claim 7, wherein the culturing step is performed at about 37° C.

12. The method of claim 7, wherein the culturing step is performed in an atmosphere containing about 5% carbon dioxide ($CO_2$).

13. The method of claim 7, further comprising the step of sub-culturing the bone cells by trypsinization after the culturing step and prior to the seeding step.

14. A method for growing bone cells, comprising the steps of:
   (a) anodizing a titanium substrate to form an array of titanium dioxide nanotubes on a surface of the titanium substrate;
   (b) subjecting the anodized titanium substrate to a radio frequency plasma discharge with a radio frequency of about 13.56 MHz to chemically modify the array of titanium dioxide nanotubes formed on the surface of the titanium substrate;
   (c) seeding bone cells onto the surface of the titanium substrate that has an array of titanium dioxide nanotubes thereon after the subjecting step; and
   (d) incubating the seeded bone cells for a period of time effective for the cells to grow and proliferate.

* * * * *